United States Patent
Lee

(10) Patent No.: US 9,833,568 B2
(45) Date of Patent: Dec. 5, 2017

(54) COMPRESSION ELEMENT DRIVEN FLUID DELIVERY APPARATUS

(71) Applicant: Freddie Eng Hwee Lee, Singapore (SG)

(72) Inventor: Freddie Eng Hwee Lee, Singapore (SG)

(*) Notice: Subject to any disclaimer, the term of this patent is extended or adjusted under 35 U.S.C. 154(b) by 300 days.

(21) Appl. No.: 14/602,624

(22) Filed: Jan. 22, 2015

(65) Prior Publication Data

US 2015/0209570 A1    Jul. 30, 2015

Related U.S. Application Data

(60) Provisional application No. 61/931,195, filed on Jan. 24, 2014.

(51) Int. Cl.

| | |
|---|---|
| *A61M 5/145* | (2006.01) |
| *F16F 1/373* | (2006.01) |
| *A61M 5/24* | (2006.01) |
| *A61M 5/20* | (2006.01) |
| *F16F 1/371* | (2006.01) |
| *F16F 1/368* | (2006.01) |

(52) U.S. Cl.
CPC ......... *A61M 5/1454* (2013.01); *F16F 1/3732* (2013.01); *A61M 5/1452* (2013.01); *A61M 2005/14573* (2013.01); *A61M 2005/2073* (2013.01); *A61M 2005/2488* (2013.01); *A61M 2209/045* (2013.01); *F16F 1/368* (2013.01); *F16F 1/371* (2013.01)

(58) Field of Classification Search
CPC ............ A61M 5/1454; A61M 5/14546; A61M 2005/14506; A61M 5/1456; A61M 5/14566; A61M 5/14586; A61M 5/14593; A61M 5/145; F16F 1/34; F16F 1/374; F16F 1/368; F16F 1/371; F16F 1/373; F16F 1/3732; F16F 1/3737; F16F 3/0876
See application file for complete search history.

(56) References Cited

U.S. PATENT DOCUMENTS 5,743,879 A * 4/1998 Kriesel ............... A61M 5/1454
                                                    128/DIG. 12
5,800,405 A * 9/1998 McPhee ............... A61M 5/1454
                                                    604/135

(Continued)

OTHER PUBLICATIONS

U.S. Appl. No. 14/602,679, filed Jan. 22, 2015, Freddie Eng Hwee Lee.

*Primary Examiner* — Imani Hayman
*Assistant Examiner* — James D Ponton
(74) *Attorney, Agent, or Firm* — Wolf, Greenfield & Sacks, P.C.

(57) ABSTRACT

The present invention relates to a medical apparatus, methods and system for fluid medication delivery. The apparatus has a drive mechanism module and a fluid container engaged to the drive mechanism. The drive mechanism includes a resilient member compressed to act against a gasket movably disposed in the fluid container. When extending to its original shape, the resilient member pushes the gasket to move inside the fluid container to eject the fluid out of the fluid container. The fluid container is connected to a flow restrictor tube that allows a predetermined flow rate of medication to be infused or injected to a patient.

19 Claims, 7 Drawing Sheets

(56) References Cited

U.S. PATENT DOCUMENTS

| | | | | |
|---|---|---|---|---|
| 6,019,747 A * | 2/2000 | McPhee | ............... | A61M 5/1454 604/136 |
| 6,348,043 B1 * | 2/2002 | Hagen | ................. | A61M 5/1452 604/131 |
| 6,712,794 B2 * | 3/2004 | Kust | .................. | A61B 17/8822 604/211 |
| 2003/0105430 A1 | 6/2003 | Lavi et al. | | |
| 2004/0210199 A1 * | 10/2004 | Atterbury | .......... | A61M 5/31566 604/224 |

* cited by examiner

COMPRESSION ELEMENT DRIVEN FLUID DELIVERY APPARATUS

CROSS-REFERENCE TO RELATED APPLICATIONS

This application claims the benefit under 35 U.S.C. §119 (e) of U.S. Provisional Application Ser. No. 61/931,195, entitled "FLUID DELIVERY DEVICE" filed on Jan. 24, 2014, the entire contents of which are incorporated herein by reference.

TECHNICAL FIELD

The present invention relates to a fluid delivery apparatus. In particular, it relates to a fluid delivery apparatus for infusion and injection of fluid medical substance.

BACKGROUND

The use of disposable elastomeric ambulatory infusion devices have gain wide acceptance due to its ease of use, safe and effective means of drug delivery in non hospital based settings. There are however limitations in situations where infusions are not required immediately after filling e.g. a patient needing multiple doses over a long duration. The filled devices that are used later may not have the intended flow rates as the pressure generated by the elastomer would typically change with time. Another drawback of known devices is the variation in pump pressure makes simultaneously multiple filling impractical, weaker pumps would fill up easily and end up with larger volume of medication than stronger pumps.

SUMMARY OF INVENTION

The disclosed invention enables multiple devices to be filled simultaneously by means of a manifold connected to a filling machine, simplifying the work in medication preparation by pharmacists. In one embodiment, the driving mechanism pushing the fluid is housed in a separate module, it is not subject to any stress with the devices when the fluid is filled into the fluid container. These devices could as a result be stored over an extended period covering the therapy duration, and be assembled to the drive mechanism only right before use, therefore the risks of changed performance of fluid medication delivery is reduced.

The invention disclosed includes a system and device setup for fixed rate infusion of medicinal fluids in which the fluid container will be engaged into a drive mechanism by rotational motion executable by manual or machine assisted means. The force generated by a resilient member provided within the drive mechanism housing for the fluid delivery is approximately constant throughout the lateral deformation and displacement of the resilient member such that intended fixed flow rates could be achieved regardless of varying volumes of the fluid in the fluid container. This enables a common drive mechanism to function with different initial fill volumes of the fluid in the fluid container, giving great benefits in an infusion environment where the fixed rate fluid flow and intended medicinal dose may necessitate a uniquely specific infusion volume. Typically, this would require the need for a wide range of receptacle volumes and invariably actuator modules to achieve the intended medication dose. This disclosed invention is uniquely different from known devices where fluid is instantaneously injected instead of infused with a preset flow rate that requires a force profile that is operable over a range of fluid volumes.

Another aspect of the invention is the means in which, during the fluid delivery process, the resilient member, e.g. a spring assembly extends into the void or cavity of the fluid container created by the displaced fluid as it is expelled from the fluid container. Uniquely different from known devices, the disclosed invention allows the filling of fluid medication to take place in a separate fluid container, hence freeing the driving mechanism from any deformational action that stores its elastic potential energy to drive the fluid delivery. The present invention permits a deformation of the resilient member in a first state when the fluid container is engaged with the drive mechanism in an interleaving manner and in a second state where the resilient member is allowed to freely move within the drive mechanism housing to eject the fluid out of the fluid container. In another embodiment, a fluid delivery apparatus also allows filling of fluid during and after the fluid container is attached to the drive mechanism.

BRIEF DESCRIPTION OF DRAWINGS

The preferred embodiments of this invention are explained by the figures, by way of sample only, in which.

DETAILED DESCRIPTION OF PREFERRED EMBODIMENTS

Figure 1A:
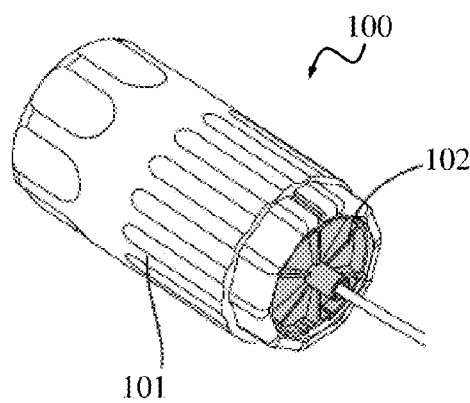
FIG. 1A is a perspective view showing a fluid delivery apparatus according to one embodiment of the present invention.

Embodiments of the present invention provide a fluid delivery apparatus, method and system for fluid medication delivery. The apparatus has a drive mechanism that pushes the fluid medication from a fluid container when the fluid container is engaged to the drive mechanism. The fluid container is connected to a flow restrictor tube that allows a predetermined flow rate of medication to be infused or injected to a patient.

The fluid container is of tubular construction within which a stopper gasket is movably disposed. The gasket separates the fluid from the drive mechanism during the fluid supply operation. The distal end of the fluid container has a port in communication with a flow restrictor tube and an in line fill fitting which together form an integral part of the fluid delivery channel to a patient. The gasket forms a chamber between the gasket and the port, for receiving and retaining a fluid therein.

To activate the fluid delivery apparatus, the fluid container is affixed to the housing of the drive mechanism. The structure of the drive mechanism and the fluid container allow the engagement of the fluid container to the drive mechanism by means of a relative rotational, transversal and/or axial movement.

The drive mechanism includes a housing and a resilient member disposed in the housing. The drive mechanism enables an approximately constant force to exert on the stopper gasket disposed in the fluid container independent of its displacement along the longitudinal axis of the housing. The coupling means integrated in the drive mechanism allows the resilient member to extend into the cavity of the fluid container as the fluid is delivered, hence reducing volume space of the device.

The disclosed invention enables ambulatory infusion or injection means with a disposable single use means, yet allowing fluid medication to be stored in the fluid container over extended duration before use.

As the fluid container and the drive mechanism are separated during the filling of the fluid into the fluid container, the apparatus could be presented as a pre-filled syringe containing the final, ready to use dose fluid medication or sterile diluents where the fluid medication can be subsequently added via the restrictor tube. The drive mechanism can be supplied directly to the hospital or other care providing sites and attached to the fluid container only when a medication infusion or injection is required, providing a significant benefit especially in situations where specific storage conditions are required for medication.

The disclosed embodiments provide solutions for ready to use, pre-filled fluid delivery apparatus and system in larger infusion volume formats, beyond the typical 60 mL syringe.

One embodiment of the disclosed fluid delivery apparatus could have an optional plunger attachable to the stopper gasket that would allow the device to be driven by an electronic syringe pump. Yet another embodiment may include flow monitoring means along the fluid channel that would give safety related feedback and alarms not available currently with mechanical self powered infusion devices.

Figure 1B:
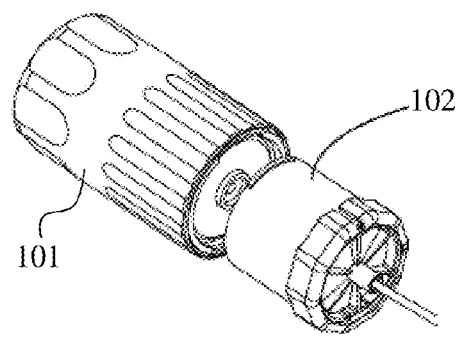
FIG. 1B is a perspective view showing the fluid delivery apparatus of FIG. 1A before the fluid container is attached to the drive mechanism.
Figure 1C:
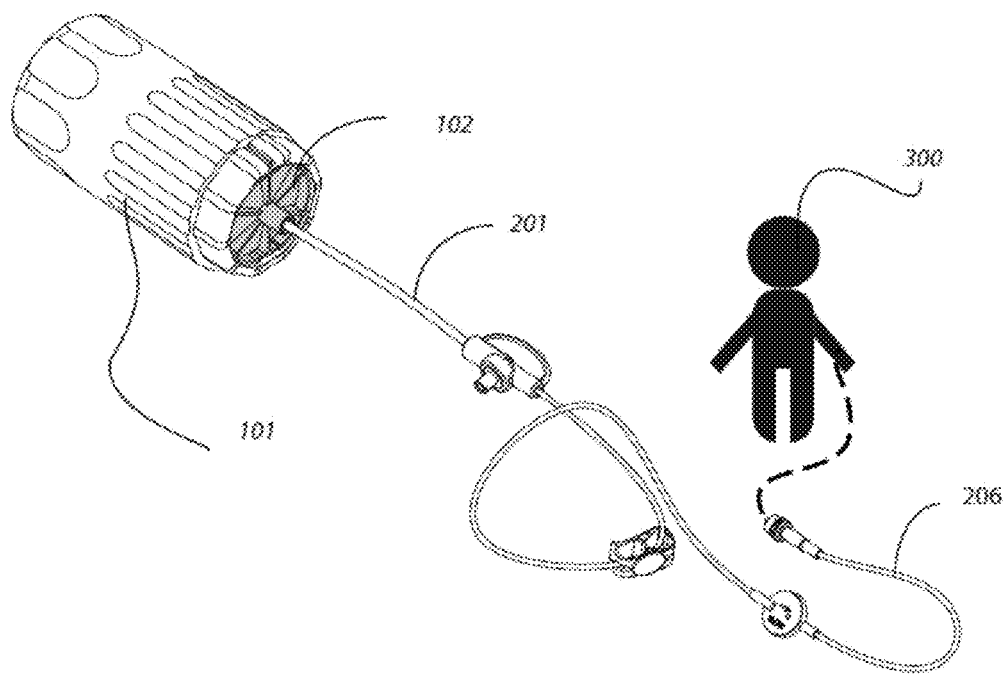
FIG. 1C shows a fluid delivery apparatus of FIG. 1A in a typical infusion set up.

Referring to FIGS. 1A, 1B and 1C, a fluid delivery apparatus 100 according to one embodiment of the invention includes a drive mechanism 101 and a fluid container 102 which may be made and prepared separately, and the fluid container 102 be attached to housing 120 of drive mechanism 101 for use. Drive mechanism 101 creates a force to cause the fluid filled in the fluid container 102 to flow through the tubes 201 which connects to the vascular system of a patient 300 by means of a catheter. The flow restrictor 206 consists of a capillary of plastic or glass, its internal diameter and length would determine the flow rate with a given pressure differential between the device and the patient's vascular pressure at the veni puncture site. This relationship is governed by Bernoulli's theorem, whereby some other factors affecting flow rate would be temperature and fluid viscosity. The fluid container maybe filled via an in-line fitting 207.

Figure 2:
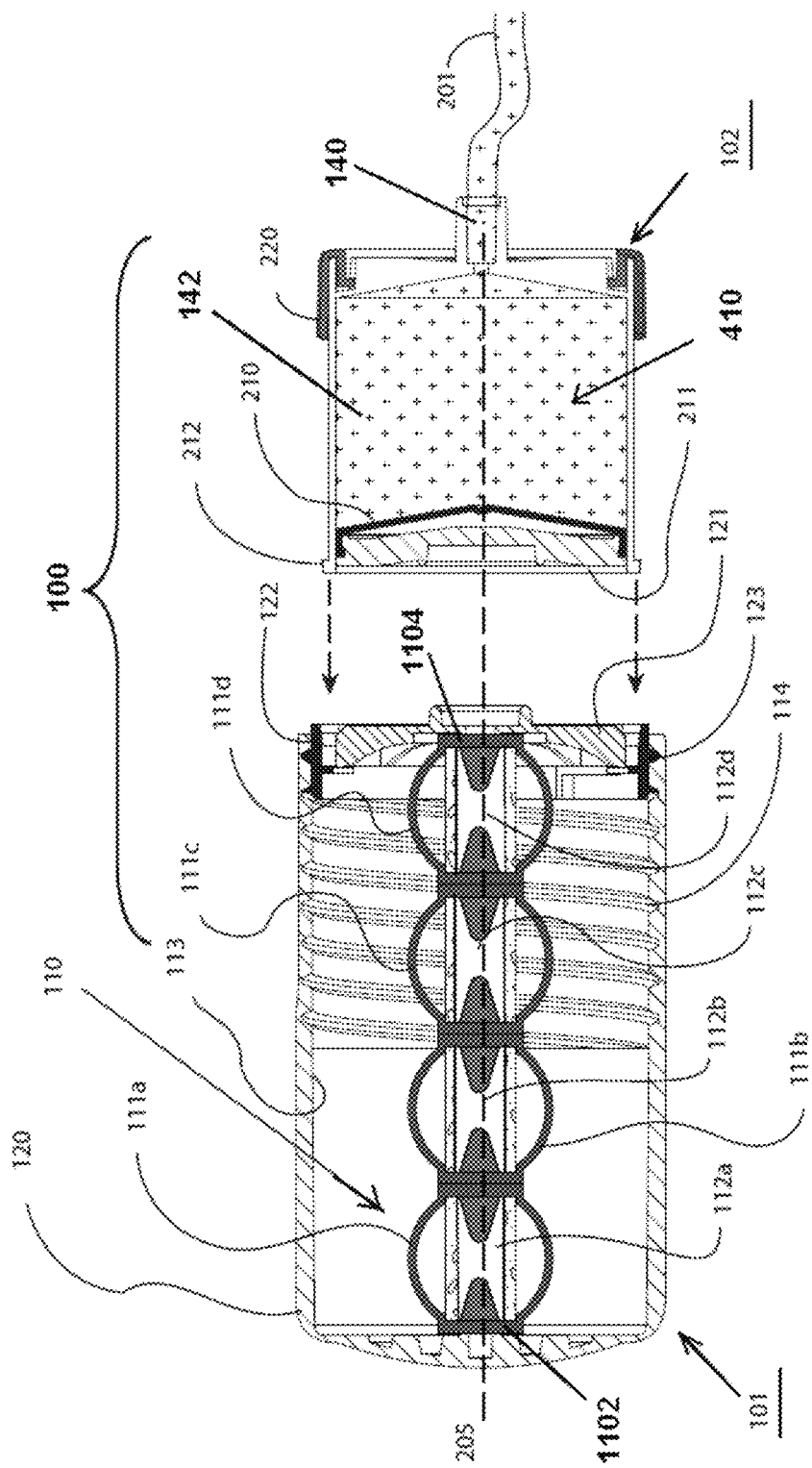
FIG. 2 is a cross-sectional view of a fluid delivery apparatus of FIG. 1A before the fluid container is attached to the drive mechanism.

Referring to FIG. 2, fluid delivery apparatus 100 includes a housing 120 and a fluid container 102 to be attached to housing 120. Fluid container 102 has a port 140 at one end through which a fluid 410 may be filled into and delivered from fluid container 102, through port 140. A gasket 210 is movably disposed in fluid container 102, forming a chamber 142 between gasket 210 and port 140 for containing the fluid 410. When port 140 is closed, the fluid is sealed in chamber 142 of fluid container 102. A resilient member 110 is disposed in housing 120. Resilient member 110 has a first end 1102 engaged to housing 120, and a second end 1104. When fluid container 102 is attached to housing 120, gasket 210 acts against second end 1104 of resilient member 110 to compress the resilient member 110 to store an elastic potential energy therein. When it is desired to deliver the fluid, port 140 is opened by which, the elastic potential energy is released such that resilient member 110 extends to resume its initial shape to push gasket 210 toward port 140, hence to eject the fluid out of chamber 142 from port 140.

Resilient member 110 includes an assembly of cylindrical sleeves 111a to 111d presenting a circumferential bending region in a radial direction. Resilient member 110 may also include tubular elements 112a to 112d each being movably installed within the space enclosed by the inner walls of a corresponding cylindrical sleeve 111a to 111d, in a manner where the axis of the tubular elements 112a to 112d lie in the plane enclosed by the circumference of the cylindrical sleeves (see FIG. 2). The cylindrical sleeves 111a to 111d and tubular elements 112a to 112d may be made of plastic material with appropriate strength and elastic properties. The repetitions of the cylindrical sleeves and tubular elements may vary according to the dimensions and other design requirements of the fluid delivery apparatus.

In one embodiment, adjacent cylindrical sleeves could be paired or connected as a single member and formed by injection molding process.

The elastic potential energy stored in a compressed cylindrical sleeve will produce a force perpendicular to the tangential plane at the point of compression biasing the cylindrical sleeve to return to its initial, uncompressed shape. For any compression, the ability to which the sleeves and tubular elements regain its initial shape depends on at least one of the parameters namely, its dimensions including wall thickness, diameter, height or depth of the cylindrical sleeve or tubular element and the elastic properties of the material used. Consequently, the displacement of any point on the cylindrical sleeve along the longitudinal axis 205 resulting from a deformation of the cylindrical sleeves and the tubular elements would also be influenced by similar factors.

Figure 3:
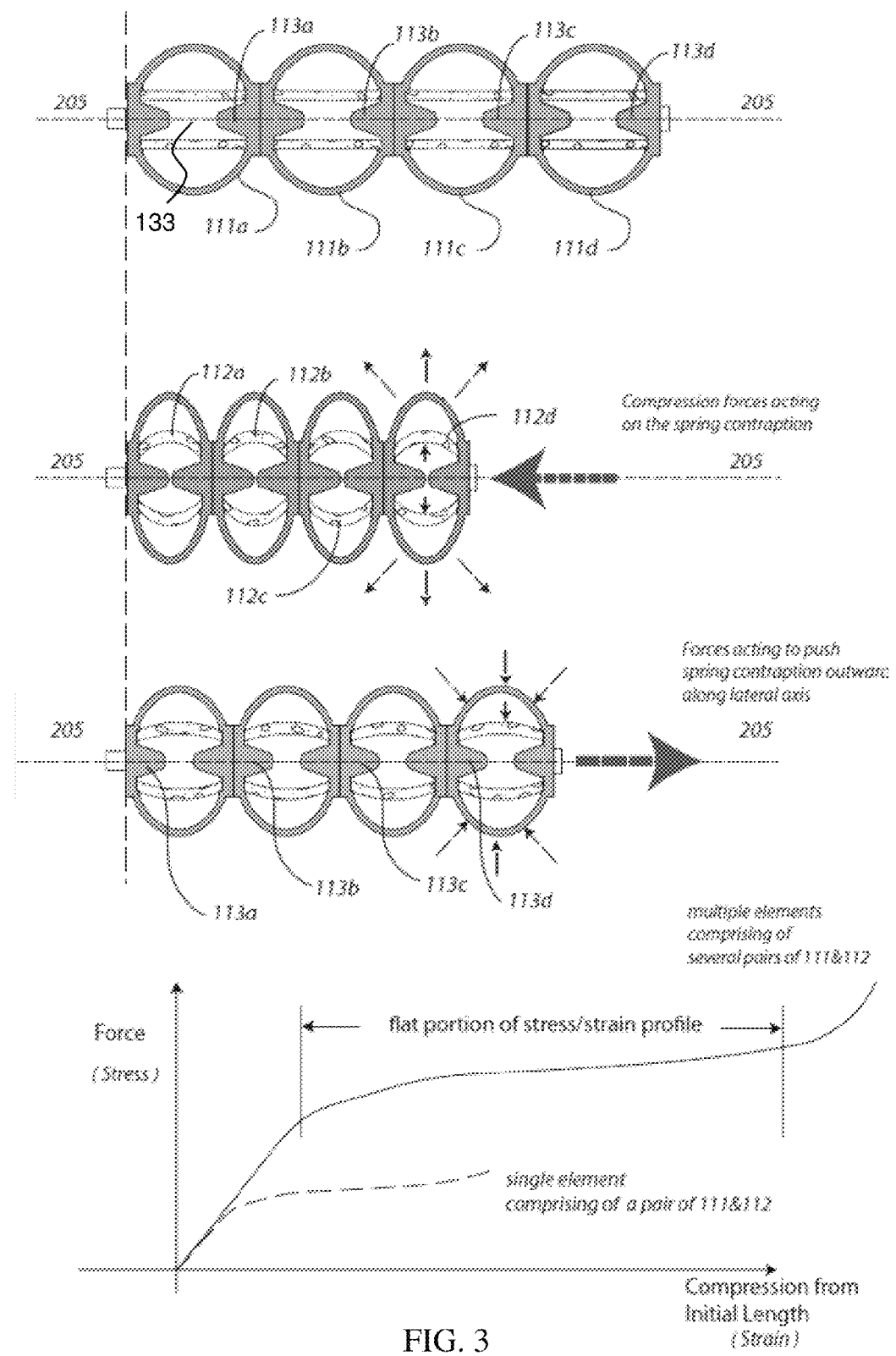
FIG. 3 is a graph that approximates the relationship between a force exerted by the resilient member of the fluid delivery apparatus of FIG. 1A and the distance the resilient member is compressed from its initial length.

Referring to FIG. 3, a pair of radial protrusions 113a to 113d maybe integrated in each of the cylindrical sleeves, projecting from an inner wall of the sleeve, and facing each other to form a gap 133 therebetween. When the cylindrical sleeves are compressed to a certain stage, the pair of protrusions in each cylindrical sleeve will be brought into contact with each other, acting as limiters to prevent over compression of the cylindrical sleeves beyond its functional elastic range. When a tubular element is disposed into a cylindrical sleeve, the pair of protrusions will be disposed within the tubular element. In this regard, protrusions 113a to 113d may also serve to prevent tubular elements 112a to 112d from being detached from the cylindrical sleeves 111a to 111d.

The longitudinal axis 205 of housing 120 formed by a longitudinal line that joins the centres of cylindrical sleeves 111a to 111d is aligned with the radial protrusions 113a to 113d originating from circumferential wall of cylindrical sleeves 111a to 111d such that tubular elements 112a to 112d could be movably assembled within a respective cylindrical sleeve 111a to 111d. The tubular elements 112a to 112d may be made from elastic material such that a compression force acting along the longitudinal axis 205 will cause a deformation of the tubular elements 112a to 112d, manifesting in a bulging of the tubular walls in an outward direction from its own longitudinal axis. When the applied compression force is removed, the tubular elements 112a to 112d in regaining its initial shape will exert an outward force towards the circumference wall of the cylindrical sleeves 111a to 111d.

Further referring to FIG. 3, the relationship between the force required to deform the resilient member including an assembly of cylindrical sleeves 111a to 111d and tubular elements 112a to 112d, and its movement along the longitudinal axis 205 or displacement from its initial state, is shown. Both components exhibit a digressive force displacement pattern where beyond a threshold, the force is approximately constant through the subsequent displacement length along the longitudinal axis 205. In addition to the aforesaid parameters that impacts the performance characteristics of the resilient member, the circumferential bending region of the cylindrical sleeves may also be shaped in any other appropriate profile, for example but not limited to, a parabolic contour such that a desired force versus displacement profile could be achieved. The disclosed embodiment offers the means to extend the flat portion of the stress strain profile of the resilient member by optimising the aforesaid parameters.

The level of the threshold force can be predetermined by varying the dimensions and choice of materials used in one or both of the cylindrical sleeves 111a to 111d and tubular elements 112a to 112d such that it ensures the drive mechanism dispense fluid out from the fluid container with minimal residual at the end of infusion.

In one embodiment of the disclosed invention, the maximum displacement/deformation range of the resilient member is limited to about 35-40% of the initial free distance predisposed by the dimensions and deformation properties of the resilient member. The considerations include but are not limited to an adequate travel distance within the receptacle cavity, no obstructions within the inner walls of the cavity and proper functioning of the drive mechanism, in particular that there is an adequate force to push the fluid out without dysfunctioning material fatigue with time.

The longer travel distance or displacement of the resilient member will help to reduce the cross sectional area of the diameter of the fluid container for any volume of fluid to be dispensed. A direct advantage derived from a longer travel distance is its contribution to the flow accuracy of the device. Furthermore, the surface area of the stopper gasket 210 in contact with the fluid could be reduced and therefore a smaller force is needed to generate a required pressure to push the fluid. The flow restrictor 206 could be dimensioned accordingly with larger inner lumen that is relatively easier to produce.

Fluid delivery apparatus 100 may further include a cap 121 rotatably attached to second end 1104 of resilient member 110. A circumferential container flange 212 formed on the external wall of fluid container 102 and a circumferential cap flange 122 on the cap 121 could be presented with features that engage with corresponding mating features, e.g. inner thread groove 114 of housing 120 that confines the relative displacement of the fluid container 102 within the housing 120, such that an intended compression force of the resilient member 110 is attained. Due to the engagement of cap flange 122 and thread groove 114, cap 121 is allowed to rotate relative to housing 120 which will cause cap 121 moving along longitudinal direction 205. When cap 121 is not rotated relative to housing 120, movement of cap 121 along longitudinal direction 205 is prevented, hence the resilient member 110 is restricted from compression and extension.

Figure 4:
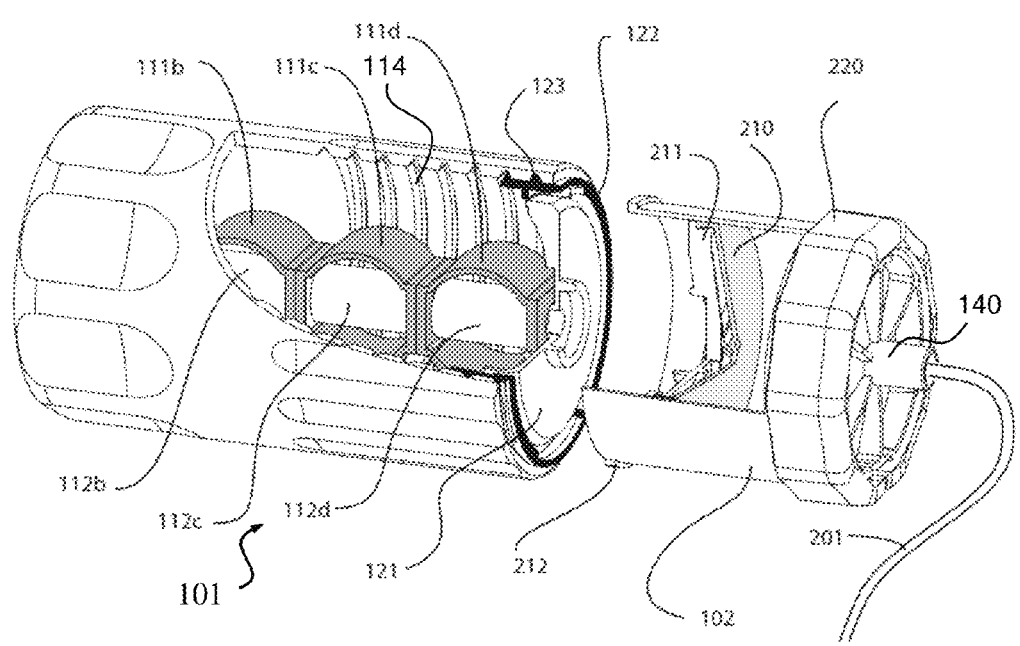
FIG. 4 is a perspective view of FIG. 1B with cut out sections showing the internal components of both the fluid container and the drive mechanism before the two modules are engaged.

Referring to FIG. 4, a perspective view with a cut out section of the drive mechanism and fluid container before engagement is presented.

In this patent application, a method of assembling a fluid delivery apparatus and disengaging the resilient member from the drive mechanism housing and enabling it to travel inside the cavity of the fluid container is disclosed.

Container flange 212 interlocks with the circumferential cap flange 122 of the retainer cap 121. Upon rotational movement of the fluid container 102 relative to housing 120, fluid container 102 will be inserted into housing 102 in an interleaving manner.

In one embodiment, a contoured cylindrical shell 220, typically made of a rigid material is optionally presented on an external wall of fluid container 102, as a means to aid better grip on the receptacle module during the above said rotational movements.

Regardless of the position of the stopper gasket 210 within the fluid container 102, which in the case of a prefilled fluid container would be determined by the volume of fluid filled, the stopper gasket 210 will contact with the retainer cap 121 of the drive mechanism and hence be subjected to forces produced by compressed resilient member when the fluid container 102 is attached to the housing 120 of drive mechanism 101 along their common radial axis.

In one embodiment, the cap 121 has protruding features on its external surface such that it could be securely attached to gasket 210 which has matching contours on its exposed surface 211. It is noted that any feature on the surfaces of cap 121 and gasket 210 that provides a firm attachment for the purpose of driving gasket 210 into the cavity of fluid container 102 during operation would be covered by this disclosure.

Circumferential cap flange 122 is perforated along its boundary of contact with cap 121. The circumferential cap flange 122 has annular screw threads 123 on its circumference that engages the thread grooves 114 formed on inner surface of housing 120, and facilitates its movement into the housing 120 when cap 121 is rotated by the rotation action of the fluid container 102 being engaged into the housing 120. The rim of the fluid container 102 is inter spaced with ridges that fitted into mating slots on the circumferential flange 122 by which fluid container 102 and cap 121 are coupled, such that rotating the fluid container 102 will cause a similar rotation of the circumferential cap flange 122. Thread grooves 114 guide the screw threads of the circumferential cap flange 122 as the cap 121 moves along longitudinal direction 205, to compress the resilient member 110. The inner side of cap 121 is rotatably affixed to the second end 1104 of the resilient member 110 with e.g. a ball and socket joint. It should be understood that other forms of mating attachment between the resilient member and the retainer cap would still function.

Figure 5:
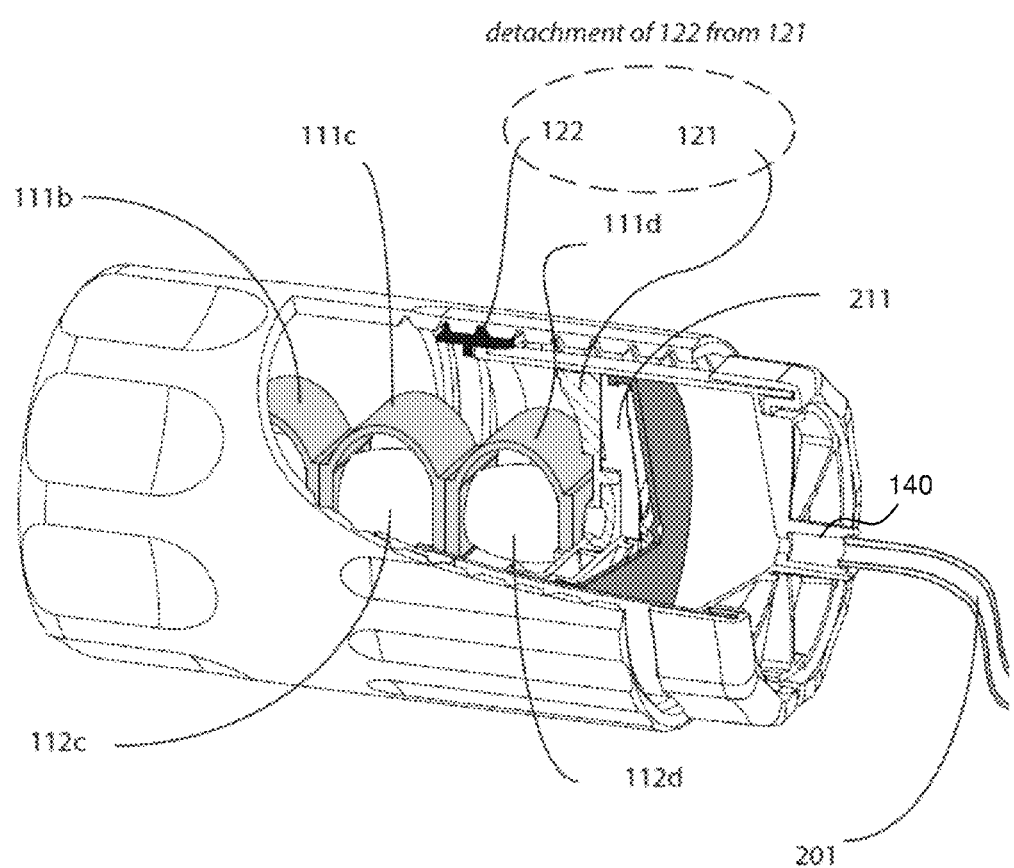
FIG. 5 is a perspective view of FIG. 1A with cut out sections showing the internal components of both fluid container and the drive mechanism interleavingly engaged.

The rotational movement of the fluid container 102 into the housing 120 results in cap 121 travelling in the direction toward the base of the housing 120. When retainer cap 121 reaches a predetermined position in housing 120, e.g. at the end of groove 114, end cap 121 will stop rotation, and the force exerted on gasket 210 along the longitudinal axis 205 toward the fluid container 102 due to the compression of the resilient member 110 and the shear forces acting tangentially on the perforated boundary of the circumferential contact with cap 121 created by its rotational movement, will cause a detachment of circumferential cap flange 122 from the main body portion of cap 121, as shown in FIG. 5.

Figure 6A:
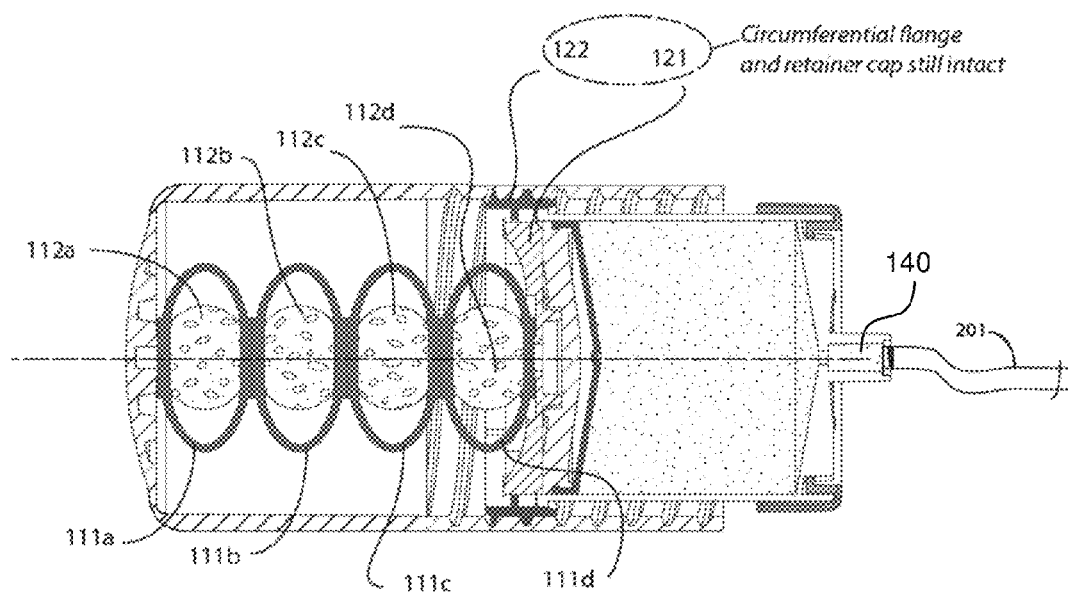
FIG. 6A and FIG. 6B are cross sectional views of the fluid container and drive mechanism during use, showing the relative positions of the resilient member within the cavity of the fluid connector.
Figure 6B:
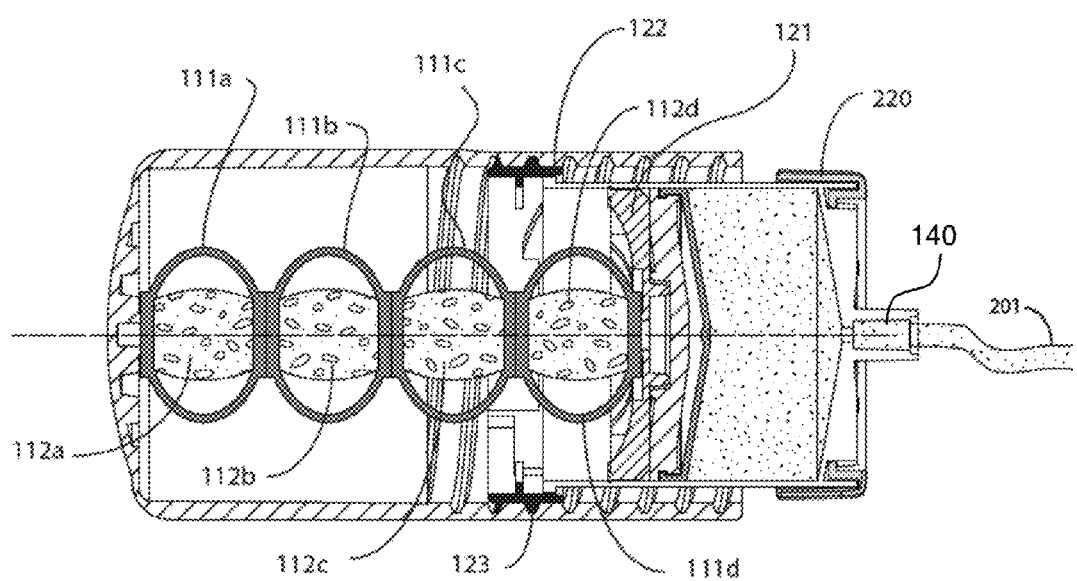

After the cap flange 122 is detached, the main body portion of cap 121 is allowed to slide inside housing 120, by which, the resilient member 110 exerts a force against gasket 210 through cap 121, as shown in FIG. 6A and FIG. 6B. When the tube 201 is connected to the distal end of fluid container 102 and port 140 is opened, the elastic potential energy stored in the resilient member 110 will be released. Resilient member 110 then pushes gasket 210 toward the port 140, to eject the fluid out of the fluid container 102 through port 140. It should be appreciated that the circumferential cap flange 122 may further include features that limits axially its position and consequently limits the axial position of the rim of the fluid container 102 within housing 120, therefore affecting the extent to which the resilient member 110 extends within the fluid container 102.

Figure 7A:
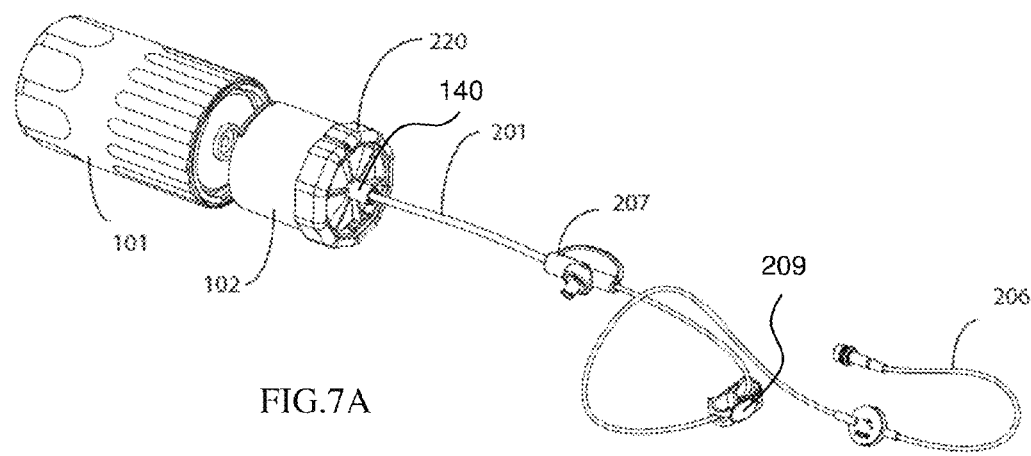
FIGS. 7A, 7B and 7C show alternate embodiments of the invention addressing different application needs.
Figure 7B:
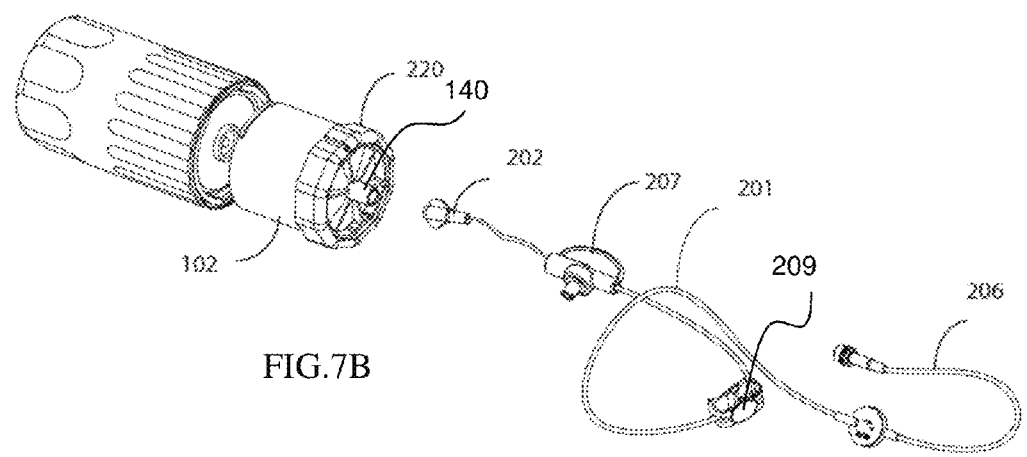
Figure 7C:
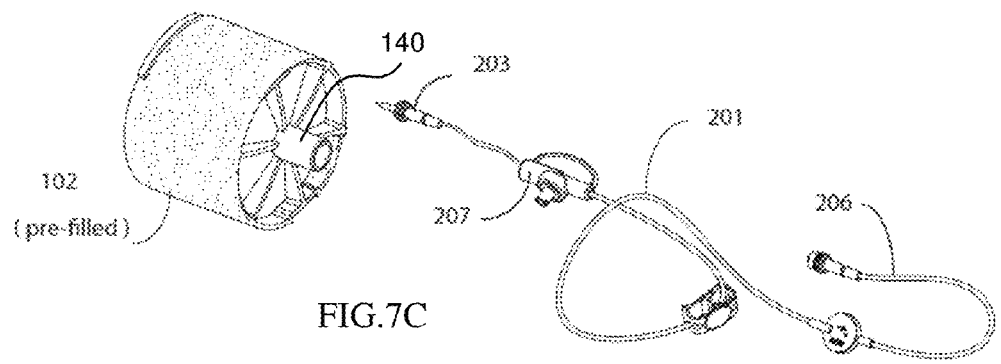

Referring to FIG. 7A, 7B and 7C, in one embodiment, the flow restrictor tube 206 dimensioned to produce a specific flow rate is pre attached to the fluid container 102, via tube 201 and a valve 209, as shown in FIG. 7A. In yet another embodiment, the flow restrictor tube 206 with a luer connector 202 and a valve 209 could be supplied separately, allowing the user to freely select a specific fixed flow rate for subsequent attachment to the fluid receptacle module, as shown in FIG. 7B. In the above embodiments, port 140 may be controlled to open by valve 209 for the fluid delivery. In yet another embodiment where the fluid container is supplied as a prefilled syringe, the flow restrictor tube 206 and its in line fill fitting may have a spiked connector 203 or any appropriate means that enables fluid communication between patient and receptacle when the tube is attached to the fluid container and when the spike connector 203 pierces into port 140.

Although embodiments of the present invention have been illustrated in conjunction with the accompanying drawings and described in the foregoing detailed description, it should be appreciated that the present invention is not limited to the embodiments disclosed. Therefore, the present invention should be understood to be capable of numerous rearrangements, modifications, alternatives and substitutions without departing from the spirit of the invention as set forth and recited by the following claims.

I claim:

1. A fluid delivery apparatus comprising:
   a housing;
   a fluid container having a port at one end thereof;
   a gasket movably disposed in the fluid container to form a chamber between the gasket and the port, wherein a fluid is filled into and sealed in the chamber;
   a resilient member having a first end and a second end, wherein the first end is capable of engaging with the housing;
   wherein when the fluid container is attached to the housing, the gasket acts against the second end of the resilient member to compress the resilient member along a longitudinal axis of the housing;
   wherein when the port is open, the resilient member is configured to extend to push the gasket toward the port to eject the fluid out of the chamber from the port;
   wherein the fluid container is movable relative to the housing toward the resilient member to compress the resilient member; and
   wherein the housing has thread grooves formed at an inner surface thereof, the fluid container has a container flange engageable to the thread groove, wherein rotation of the fluid container causes the fluid container to move relative to the housing along the longitudinal axis toward the resilient member to compress the resilient member; and
   a cap disposed between the resilient member and the gasket, the cap having a main body portion rotatably attached to the second end of the resilient member and a cap flange engaged to the thread groove, wherein when the cap is stationary relative to the housing, the resilient member is restricted from compression and extension.

2. The apparatus of claim 1, wherein when the fluid container rotates relative to the housing, the gasket pushes the cap toward the first end to compress the resilient member, and wherein when reaching a predetermined position, the cap flange is separated from the main body portion such that the cap is slidable within the housing to allow the resilient member to act against the gasket through the cap.

3. The apparatus of claim 2, wherein the resilient member includes one or more elastically deformable sleeves arranged in series and with a radial direction of each sleeve in alignment with the longitudinal axis of the housing, wherein when the resilient member is compressed along the longitudinal axis, each sleeve is compressed along the radial direction.

4. The apparatus of claim 3, wherein each sleeve further comprises a pair of protrusions extending from an inner wall of the sleeve along the radial direction and facing each other, the pair of protrusions forming a gap therebetween to allow compression of the sleeve and when the pair of protrusions are in contact against each other, the sleeve is prevented from being further compressed.

5. The apparatus of claim 3, further comprising one or more elastically deformable tubular elements each being disposed in one of the sleeves with an axial direction of each tubular member in alignment with the longitudinal axis of the housing, wherein when the resilient member is compressed, each tubular member is compressed along the axial direction.

6. The apparatus of claim 5, wherein each sleeve further comprises a pair of protrusions extending from an inner wall of the sleeve along the radial direction and facing each other, the pair of protrusions forming a gap therebetween to allow compression of the sleeve, wherein the pair of protrusions of each sleeve are disposed within the tubular member in the sleeve to prevent the tubular member from being detached from the sleeve.

7. The apparatus of claim 1, further comprising a valve connected to the port to control the closing and opening of the port.

8. The apparatus of claim 7, further comprising a luer connector connected to the port for attaching a fluid channel thereto.

9. The apparatus of claim 1, the port being pierceable by a spike connector to open the port for fluid delivery.

10. A fluid delivery apparatus comprising:
    a housing;
    a fluid container having a port at one end thereof;
    a gasket movably disposed in the fluid container to form a chamber between the gasket and the port;
    a resilient member having a first end engaged to the housing and a second end acting against the gasket,
    wherein when a fluid is filled in the chamber and the port is closed, and when the fluid container is attached to the housing, the gasket acts against the second end of the resilient member to compress the resilient member along a longitudinal axis of the housing;

wherein when the port is open, the resilient member is configured to extend to push the gasket toward the port to eject the fluid out of the chamber from the port;

wherein the fluid container is movable relative to the housing to compress the resilient member;

wherein the housing has thread grooves formed at an inner surface thereof, the fluid container has a container flange engageable to the thread groove, wherein rotation of the fluid container causes the fluid container moving relative to the housing along the longitudinal axis to compress the resilient member; and a cap disposed between the resilient member and the gasket, the cap having a main body portion rotatably attached to the second end of the resilient member and a cap flange engaged to the thread groove, wherein when the cap is stationary relative to the housing, the resilient member is restricted from compression and extension.

11. The apparatus of claim 10, wherein when the fluid container rotates relative to the housing, the gasket moves the cap toward the first end to compress the resilient member, and wherein when reaching a predetermined position, the cap flange is separated from the main body portion such that the cap is slidable within the housing to allow the resilient member to act against the gasket through the cap.

12. The apparatus of claim 10, wherein the resilient member includes one or more elastically deformable sleeves arranged in series and with a radial direction of each sleeve in alignment with the longitudinal axis of the housing, wherein when the resilient member is compressed along the longitudinal axis, each sleeve is compressed along the radial direction.

13. The apparatus of claim 12, wherein each sleeve further comprises a pair of protrusions extending from an inner wall of the sleeve along the radial direction and facing each other, the pair of protrusions forming a gap therebetween to allow compression of the sleeve, and when the pair of protrusions are in contact against each other, the sleeve is prevented from being further compressed.

14. The apparatus of claim 12, further comprising one or more elastically deformable tubular elements each being disposed in one of the sleeves with an axial direction of each tubular member in alignment with the longitudinal axis of the housing, wherein when the resilient member is compressed, each tubular member is compressed along the axial direction.

15. The apparatus of claim 14, wherein each sleeve further comprises a pair of protrusions extending from an inner wall of the sleeve along the radial direction and facing each other, the pair of protrusions forming a gap therebetween to allow compression of the sleeve, wherein the pair of protrusions of each sleeve are disposed within the tubular member in the sleeve to prevent the tubular member from being detached from the sleeve.

16. The apparatus of claim 10, further comprising a valve connected to the port to control the closing and opening of the port.

17. The apparatus of claim 16, further comprising a luer connector connected to the port for attaching a fluid channel thereto.

18. The apparatus of claim 10, the port being pierceable by a spike connector to open the port for fluid delivery.

19. A method for assembling a fluid delivery device, the method comprising:

filling a fluid into a fluid container, wherein the fluid container has a gasket movably disposed therein and a port formed at one end, the gasket and the port form a chamber into which the fluid is filled and retained when the port is closed;

disposing a resilient member in a housing;

attaching a cap to the resilient member, wherein the cap has a main body portion rotatably attached to the resilient member and a cap flange rotatably engaged to the housing;

attaching the fluid container to the housing and to engage the cap, rotating the fluid container relative to the housing to move the fluid container along a longitudinal axis of the housing, wherein the cap rotates relative to the housing following the rotation of the fluid container and moves along the longitudinal axis to compress the resilient member;

advancing of the fluid container relative to the housing along the longitudinal axis to separate the main body portion from the cap flange whereby the resilient member is allowed to extend along the longitudinal axis and act against the gasket through the main body portion of the cap.

* * * * *